(12) United States Patent
Barthold

(10) Patent No.: US 8,591,520 B2
(45) Date of Patent: Nov. 26, 2013

(54) APPARATUS FOR INSERTING CATHETERS OR ENDOSCOPIC DEVICES INTO A BODY CAVITY

(75) Inventor: Franz-Peter Barthold, Balingen (DE)

(73) Assignee: JOTEC GmbH, Hechingen (DE)

(*) Notice: Subject to any disclaimer, the term of this patent is extended or adjusted under 35 U.S.C. 154(b) by 382 days.

(21) Appl. No.: 13/088,163

(22) Filed: Apr. 15, 2011

(65) Prior Publication Data

US 2011/0264105 A1 Oct. 27, 2011

(30) Foreign Application Priority Data

Apr. 22, 2010 (DE) ...................... 20 2010 006 133 U

(51) Int. Cl.
*A61F 11/00* (2006.01)

(52) U.S. Cl.
USPC ...................................... 606/108; 604/167.01

(58) Field of Classification Search
USPC ............. 606/108, 191, 194, 205; 604/167.01, 604/175, 256
See application file for complete search history.

(56) References Cited

U.S. PATENT DOCUMENTS

| | | | |
|---|---|---|---|
| 5,000,745 A * | 3/1991 | Guest et al. .................... | 604/256 |
| 5,300,035 A | 4/1994 | Clement | |
| 5,366,478 A * | 11/1994 | Brinkerhoff et al. .......... | 606/213 |

* cited by examiner

*Primary Examiner* — Victor Nguyen
(74) *Attorney, Agent, or Firm* — Casimir Jones SC

(57) ABSTRACT

An apparatus for inserting an elongated device into a body cavity has a valve having a longitudinal axis. The valve is provided with a housing having a cup-shaped recess and a base, a first channel section provided in said base, a plunger having an end face, said plunger being at least with its end face inserted into and displacable within the cup-shaped recess, a second channel section provided in the plunger, and a hollow cylindrical elastic seal arranged within the cup-shaped recess between said base and said end face, said seal having an outer face and an inner face defining there between a cross section of the seal, a third channel section provided in the seal and surrounded by the inner face. The third channel section forms together with the first channel section and the second channel section a central channel, said central channel extending and being continuous along said longitudinal axis. Said seal is provided with a change in said cross section in a region along said longitudinal axis.

17 Claims, 7 Drawing Sheets

APPARATUS FOR INSERTING CATHETERS OR ENDOSCOPIC DEVICES INTO A BODY CAVITY

CROSS-REFERENCE TO RELATED APPLICATION

This application claims the benefit of German Patent Application No. DE 20 2010 006 133.4, filed Apr. 22, 2010, which is hereby incorporated by reference.

BACKGROUND

1. Field

The present invention relates to an apparatus for inserting catheters or endoscopic devices into a body cavity, the apparatus having a valve, which is provided with a housing with a cup-shaped recess bounded by a base, wherein a first channel section is provided in the base of the recess, with a plunger with an end face, wherein the plunger can at least in part be inserted into the cup-shaped recess and wherein a second channel section is provided in the plunger, and with an elastic seal arranged within the cup-shaped recess, wherein a third channel section is provided in the seal, wherein said third channel forms together with the first channel section in the base of the recess of the housing and the second channel section in the plunger a central channel, which central channel is continuous along a longitudinal axis.

2. Related Prior Art

Such introduction shuttle systems or trocars, which, for example, are used for vascular accesses or in endoscopic operations, are well-known from the prior art.

By way of example, U.S. Pat. No. 5,300,035 describes a trocar of the type mentioned at the outset, in which a proximal sealing mechanism is provided. This sealing mechanism is formed by a Tuohy-Borst valve.

The valve consists of a cup-shaped housing with a cup base and a screw top, which closes off the housing at the cup opening facing away from the cup base. In the direction of the cup base, the screw top has a plunger, which butts against an elastic seal accommodated in the housing. Here, the elastic seal is clamped between the cup base and the end face of the plunger. A central channel, formed by a plurality of channel sections, is routed through the cup base, the elastic seal and the plunger.

If the screw top is screwed into the housing, as a result of which the plunger is moved in the direction of the cup base, the seal situated between cup base and plunger is deformed such that the central channel is narrowed such that the inner diameter thereof is reduced.

Thus, such a sealing mechanism allows the formation of openings with variable diameters, which can then tightly seal an endoscopic instrument or a catheter routed through the central channel in relation to the environment or in relation to an internal liquid pressure or gas pressure. A disadvantage of the known introduction sheath is that leaks may occur as a result of the described embodiment of the valve.

This is because the constriction of the channel running through the seal, which constriction is required for the sealing effect, is based solely on the elastic deformation of the seal.

If the seal is compressed along its longitudinal axis, it is deformed such that there is a thickening in the wall. Since the walls of the cup-shaped recess restrict a radial expansion of the seal towards the outside, the thickening of the wall acts in the direction of the inner diameter of the seal, as a result of which the third channel section, running in the interior of the seal, narrows.

The seal material can thus in an interlocking fashion butt against a device, for example a catheter, situated in the interior of the channel, as a result of which the third channel section is sealed in relation to the inserted device.

In the process, a disadvantage of the known and other apparatuses with conventional Tuohy-Borst valves is that this only allows a relatively small constriction of the third channel section.

This emerges from the fact that the conventional seals, arranged in a Tuohy-Borst valve, are relatively stiff in the longitudinal direction, and so a high deformation resistance has to be overcome during the compression along the longitudinal axis; moreover, this resistance increases as the third channel section becomes ever narrower.

Thus, much force needs to be exerted for the compression in the known apparatuses in order to bring about an appreciable constriction of the channel.

A further disadvantage here is that only part of the force exerted to twist the screw top in relation to the cup-shaped housing acts in the longitudinal direction on the seal. As a result of the deformation resistance of the seal, there is gradually increasing friction between seal and screw top with increasing degree of constriction. In order to continue closing the valve, this friction must be overcome in addition to the increasing deformation resistance of the seal.

After a certain degree of constriction, the forces to be overcome become so large that a secure seal can no longer be ensured.

The above-described effect becomes even more pronounced if an asymmetric device, or an asymmetrically deformable device, for example a catheter with an off-centred guide wire, is routed through a conventional apparatus with a Tuohy-Borst valve.

This is because the seal contacts the regions of the device first that have the greatest extent perpendicular to the longitudinal axis. In the process, forces build up between the device and the seal that counter further closing of the seal. Thus, there is no sealing abutment between seal and catheter at those points on the catheter that have a smaller extent perpendicularly to the longitudinal axis.

However, leaks should be avoided for functional and medical considerations. On the one hand, bodily fluids, such as blood, can leak out through such leaks and thus adversely affect the handling or functionality of the introduction sheath and can also result in unnecessary additional contamination of the surgical surroundings, including an increased risk of infection for the operator. On the other hand, contaminants can also penetrate into the interior of the sheath shell through such leaks and may, for example, cause septic complications.

In the case of trocars, such leaks can result in a gas leak, particularly in the case of ventilating the abdominal cavity, and so the success of endoscopic operations on the internal organs is jeopardized or the complication rate is increased.

As a consequence of this, either the operator must select a very narrow valve at the very beginning, as a result of which the selection of catheters or endoscopic devices to be used is severely limited, or a valve with a larger inner diameter is selected, which may then, in certain circumstances, not be able to ensure a complete seal.

A further disadvantage of the known apparatuses lies in the difficult handling thereof.

While the operator must, on the one hand, as far as possible keep the position of the apparatus constant, a two-handed operation of the screw valve is required at the same time, for example when a catheter or an endoscopic device is inserted.

Thus, depending on the situation, two people are required in order to be able to operate the conventional apparatuses safely.

SUMMARY

In view of the above, the invention is based on the object of improving the apparatus of the type mentioned at the outset to the extent that an increased sealing property of the valve is ensured and that simpler handling of the valve is made possible at the same time.

In the apparatus of the type mentioned at the outset, this object is achieved by the fact that, in a region along the longitudinal axis of the seal, said seal has a change in cross section.

In the present case, a "region with a change in cross section" is understood to be a spatially delimited reduction or increase in the wall thickness or the inner or outer diameter of the seal.

A reduction in the wall thickness, particularly by reducing the outer diameter, leads to a partial weakening of the wall. It follows that the wall region weakened thus can be compressed more strongly if the same amount of force is exerted, which leads to an improved sealing effect.

Conversely, a spatially delimited increase in the wall thickness, particularly by reducing the inner diameter, likewise leads to a reduction in the force needed to be exerted for narrowing the seal in the case where the size of the opening through which the catheter or the endoscopic device is inserted remains unchanged. This is because, in the region of the wall thickening, the catheter is already guided in a more "taught" fashion through the channel region with the reduced inner diameter, and so a smaller deformation is required to obtain sufficient sealing.

Furthermore, provision is made for embodying the region with a changing cross section such that although the wall thickness is substantially uniform throughout, the seal overall is subjected to a change in its inner and outer diameter in a restricted region.

In this case, the deformation forces in the region of the wall are increased in the direction of the modified diameter, and so an inward or outward movement, which supports the thickening of the wall due to compression, is created.

Hence, the obtained narrowing of the inner diameter is more pronounced relative to the exerted force than in the case of conventional seals.

This is based on the fact that the seals previously used in a Tuohy-Borst valve have a substantially unchanging wall thickness all along the longitudinal direction.

As a result of the region with a changing cross section provided according to the invention, less force has to be exerted in the novel apparatus in order to seal the valve securely, and so now a one-handed operation is also possible. With the new apparatus, the third channel section may have a diameter of up to 10 mm, preferably in the range of up to 8 mm, with secure closing still being guaranteed.

Hence, the object underlying the invention is achieved in its entirety.

According to further objects of the invention, the region of the seal with a change in cross section is formed by a circumferential groove on the outer face of the seal and/or by a circumferential web on the inner face of the seal.

A weakened zone is produced as a result of a circumferential groove provided in the region of the outer face of the seal and it results in increased compressibility in this region. Here, the deformation forces are deflected perpendicularly to the longitudinal axis of the seal in the direction of the central channel. As a result, the amount of force required to seal the central channel is reduced.

If a circumferential web is provided on the inner face, this results in the above-described reduction in the force to be exerted for sealing as a result of the inner diameter in the region of the web being reduced in relation to the diameter of the opening (in the uncompressed state).

If provision is made (at the same level or height along the longitudinal axis) for both a groove in the outer face and a web on the inner face of the seal, the web, in the case of compression of the seal, is advanced in the direction of the channel as a result of the elastic deformation in the region of the groove. In addition to the above-described effects, this leads to a type of synergetic effect; the groove in the outer face so to speak pushes the web radially inwards when the seal is compressed in the direction of the longitudinal axis, which leads to a good sealing effect with little force expenditure.

Compared to the known apparatuses, this results in substantially increased narrowing of the central channel in relation to the longitudinal compression, and hence in a significant decrease in the force required for sealing.

According to another object, the known apparatus and/or the new apparatus has means for displacing the plunger relative to the housing along the longitudinal axis, without changing the circumferential orientation of the plunger relative the housing.

The advantage here is that the seal is compressed by a linear motion by means of such means for displacing the plunger. This is substantially more ergonomic than a screwing motion. Hence, a reliable one-handed operation of the apparatus is also possible under surgery conditions.

Hence, this measure even on its own, that is to say with the generic apparatus but without the cross-sectional change in the seal, involves an inventive step over a generic apparatus. Also with this embodiment of the new apparatus, the third channel section may have a diameter of up to 10 mm, preferably in the range of up to 8 mm, with secure closing still being guaranteed.

According to a particular object, the means have an actuation element, connected to the plunger, with a grip and have a grip provided on the housing, with the actuation element and the housing being moveably mounted in relation to one another. In this context, it is moreover preferred if the grips are provided on arms that act as levers.

An advantage of such an embodiment, which substantially corresponds to the design of a surgical clamp, is that little force can exert a relatively large compressive pressure on the seal via the levers. Hence, it is comparatively simple to obtain a completely tight seal.

It is also advantageous that the novel apparatus can be operated substantially quicker than is the case in conventional apparatuses. Both sealing and releasing the apparatus can be brought about in a single handling step and without needing to change the grip.

Furthermore, the handling of such an apparatus corresponds, as far as possible, to the conventional clamps, which are often used by surgeons. Hence, the operator can use the apparatus intuitively and without much familiarization.

According to a further object, the actuation element is moveably arranged about at least one axis in relation to the plunger.

This is because this can prevent the change in angle, experienced by the actuation element in relation to the cup-shaped housing during the actuation by pivoting towards the first grip, from also acting on the plunger and hence on the end face.

If the end face of the plunger were to have an angle deviating from the base of the recess provided in the housing when moving in the direction of the housing, it would compress the seal asymmetrically.

Such an asymmetric compression would lead to an uneven deformation and hence, potentially, to leaks between the seal and the inserted object, e.g., a catheter.

Since the plunger is moveably mounted in the aforementioned embodiment, it is aligned parallel to the seal and the base of the recess by the compressive resistance acting on the end face. This makes it possible to avoid an uneven compression of the seal, as a result of which a stronger sealing action is ensured.

According to another object, the guide means are provided on the housing and the plunger, which guide means hold the plunger relative to the housing in a stable alignment parallel to the longitudinal axis.

Here, it is advantageous that the plunger can be moved relative to the housing along the longitudinal axis without changing its alignment in relation to the housing. This prevents the plunger from jamming in the housing or the seal from being compressed asymmetrically.

According to a further object, the apparatus furthermore has an arresting arrangement for arresting the plunger in relation to the housing at least one position along the longitudinal axis. Here, it is particularly preferred if the arresting arrangement is provided on the grips and/or the arms.

Here, the arresting arrangement is typically embodied as a locking device with a toothing and a locking means. The toothing preferably has sliding faces and undercut locking faces, while the locking means is designed to engage in the undercut formed by the locking faces. The locking means can also be embodied as a toothing running opposite to the first toothing.

Here, this arresting arrangement can either be provided directly on the plunger and on the parts of the housing directly abutting the plunger; however, it may also be provided on the means for displacing the plunger.

In the latter case, the arresting of the means in a fixed angular position in relation to one another leads to the plunger being fixed indirectly in relation to the housing as a result of its connection to the actuation element.

The advantage of such an embodiment lies in the fact that independent displacement of the plunger, for example as a result of the expansion of the seal, is prevented.

Thus, the user need not hold the apparatus, more particularly the actuation element, permanently after actuation in order to ensure the permanent tightness of the apparatus.

Further advantages emerge from the description and the attached drawings.

It is understood that the aforementioned features, and the features still to be explained below, can be used not only in the respectively specified combinations, but also in other combinations or on their own, without departing from the scope of the present invention.

BRIEF DESCRIPTION OF THE DRAWINGS

An embodiment of the invention is illustrated in the drawing, in which.

DESCRIPTION OF A PREFERRED EMBODIMENT

Figure 1:
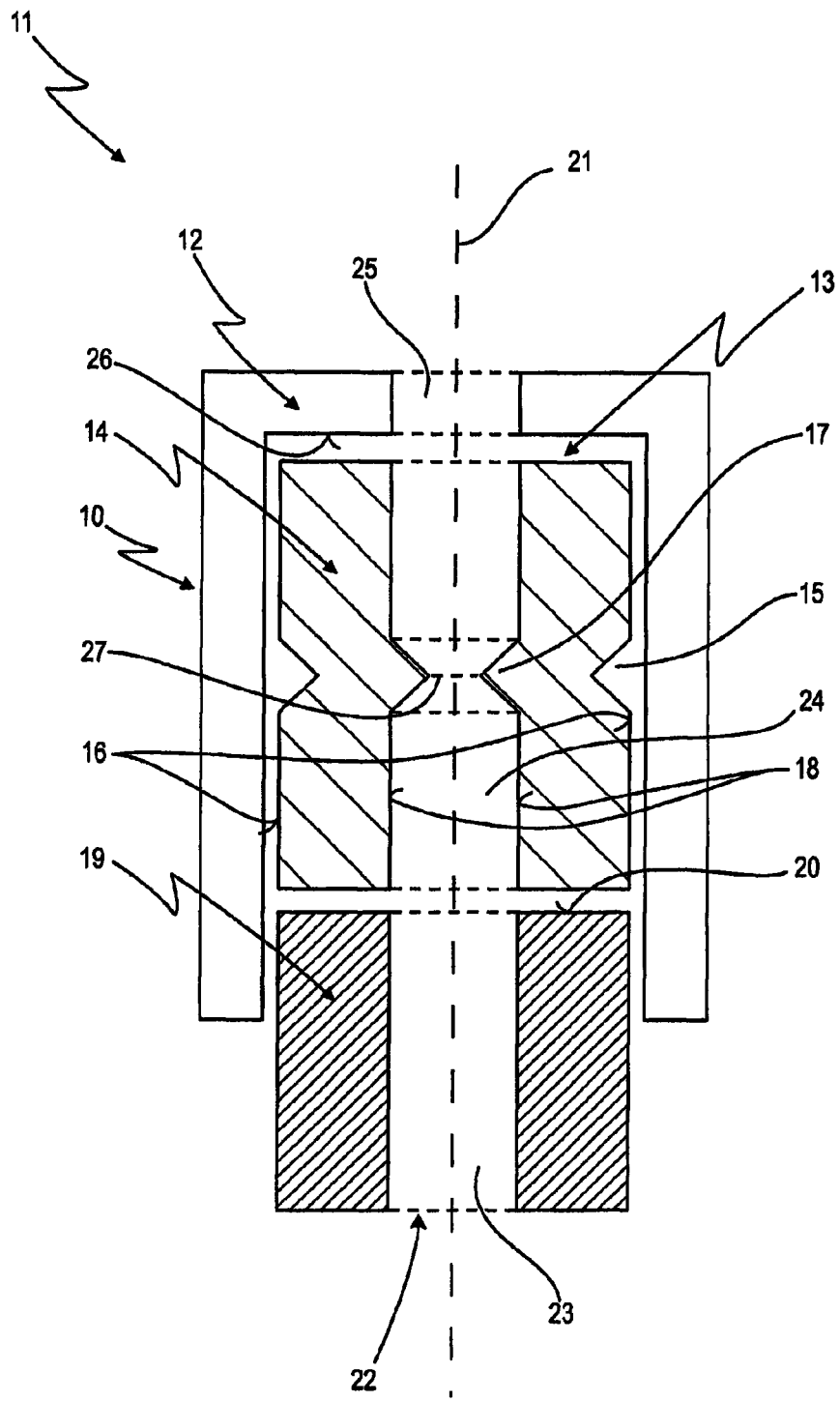
FIG. 1 shows a schematic illustration of an embodiment of a valve of the novel apparatus in a longitudinal section.

FIG. 1 shows a schematic illustration of the valve 10 of a novel apparatus 11, in a longitudinal section.

The valve 10 has a housing 12 with a cup-shaped recess 13, a hollow-cylindrical seal 14 with a groove 15 in the outer face 16 thereof and a circumferential web 17 on the inner face 18 thereof, and a hollow-cylindrical plunger 19 with an end face 20. The seal 14 is formed from an elastically yielding material, and so it can spring back into its unloaded position.

The inner and outer faces 18, 16 define between them a cross section of the seal 14, which cross section has a change at the level of the groove 15 and the web 17, which groove 15 and web 17 are arranged at the same height of a longitudinal axis 21 of the valve 10.

A channel 22 routed through the valve 10 is formed along a longitudinal axis 21 of the valve 10, which channel is formed by a channel section 23 in the region of the plunger 19, a channel section 24 in the region of the seal 14 and a channel section 25 in the region of a base 26 of the cup-shaped recess 13. The channel 22 has an opening 27 in the region of the web 17 of the seal 14. This opening 27 has a diameter of less than 10 mm, preferably of up to 8 mm.

In order to close the valve, the end face 20 of the plunger 19 is pressed against the seal 14, as a result of which the seal 14 jams between the end face 20 and the base 26 of the cup-shaped recess 13 and is subsequently compressed along the longitudinal axis 21.

Figure 2:
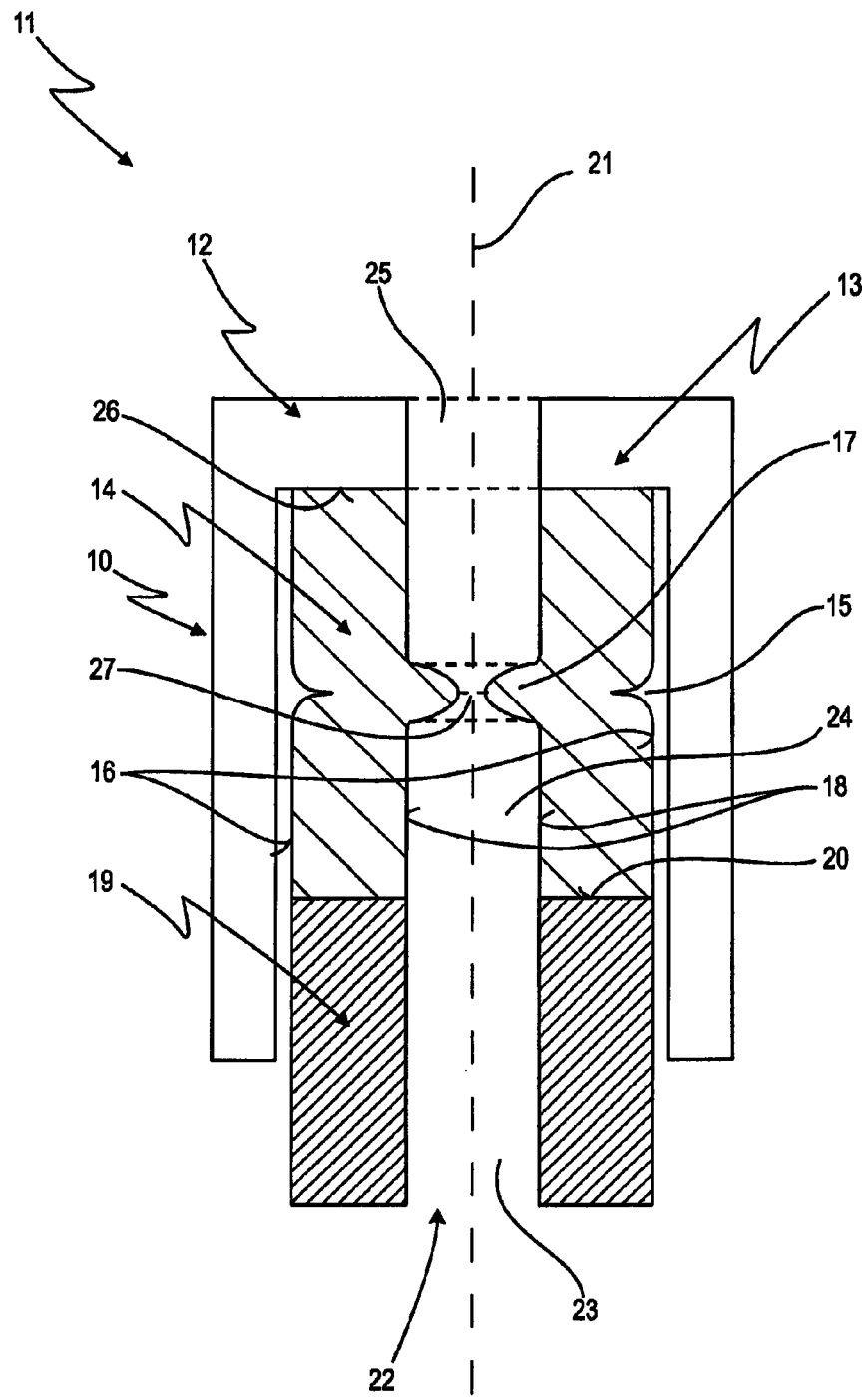
FIG. 2 shows a schematic illustration of the valve as in FIG. 1, but with a partly compressed seal.

FIG. 2 shows the valve 10 from FIG. 1 with a partly compressed seal 14.

As a result of the compression of the seal 14 along the longitudinal axis 21, there is a gradual inwards movement of the web 17 of the seal 14, as a result of which the opening 27 gradually becomes ever narrower and is finally closed. Conversely, moving the plunger 19 away from the base 20 of the cup-shaped recess 13 gradually releases the seal 14, as a result of which it can extend in the longitudinal direction, the web gradually returns to its initial position and the opening 27 gradually dilates.

Figure 3:
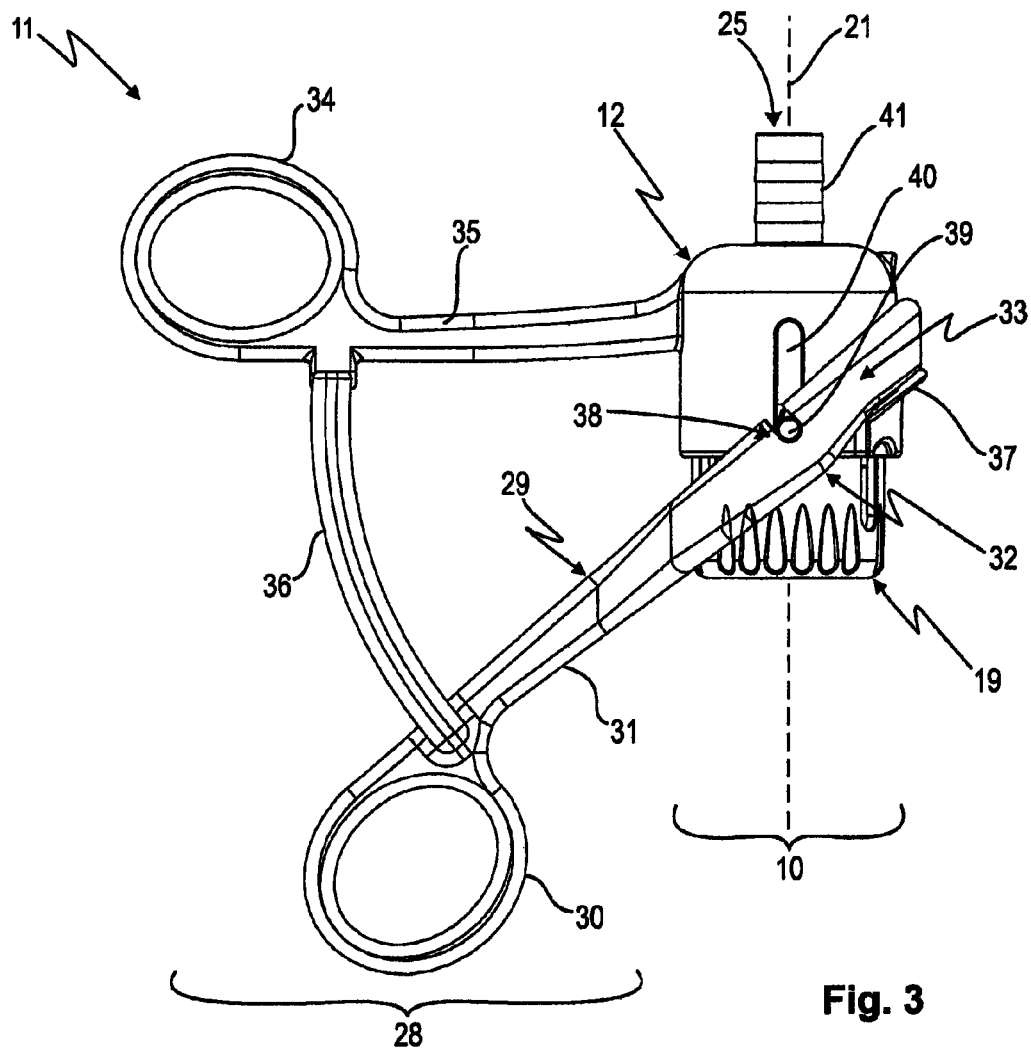
FIG. 3 shows a schematic illustration of an embodiment of the novel apparatus in a lateral view.

FIG. 3 shows a lateral view of a schematic illustration of an embodiment of the novel apparatus 11. In addition to the valve 10 with the plunger 19, the housing 12 and the seal (not illustrated), the apparatus 11 comprises means 28 for displacing the plunger 19 relative to the housing 12 along the longitudinal axis 21.

The means 28 consists of an actuation element 29 with a grip 30, which is connected via an arm 31 to a ring 33 forming an opening 32. The ring 33 surrounds the valve 10 in the circumferential direction. At the housing 12, the means 28 furthermore have a grip 34, which is connected to the housing 12 via an arm 35.

An arresting arrangement 36 is formed between the arm 31 and the arm 35 and it affords the possibility of arresting the actuation element 29 along different angular positions relative to the housing 12. In this context, a bead 37 provided on the housing 12 serves as a support on which the ring 33 is supported.

The actuation element 29 is furthermore moveably connected to the plunger 19 via recesses 38, wherein pins 39 provided on the plunger 19 are held in the recesses 38 and run in recesses 40 provided in the housing 12 when the plunger 19 is moved in the direction of the longitudinal axis 21.

The housing 12 moreover has a nozzle 41, which elongates and radially delimits the channel section 25.

Figure 4:
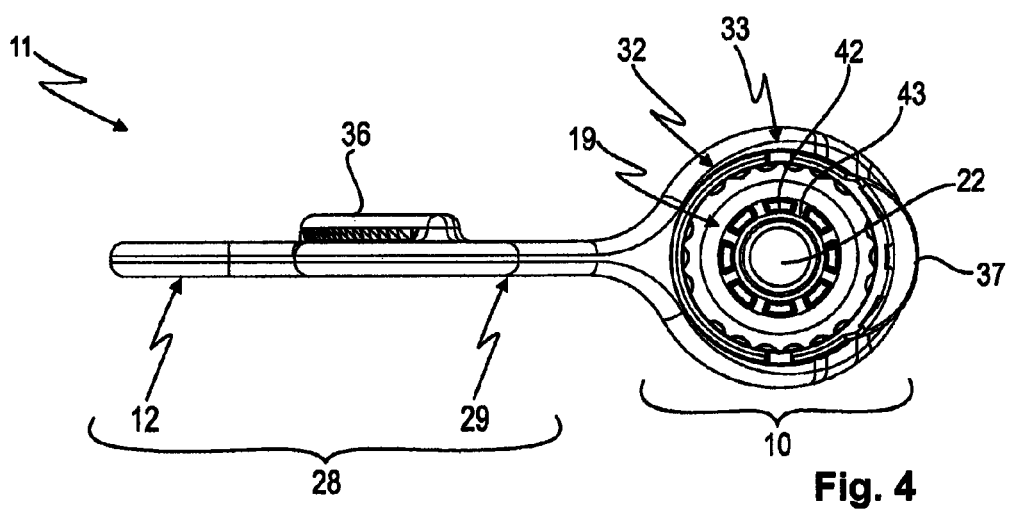
FIG. 4 shows a schematic illustration of the embodiment of the novel apparatus as per FIG. 3 in a plan view.

FIG. 4 shows a plan view of the embodiment of the novel apparatus 11 from FIG. 3 with the valve 10 and the means 28 for displacing the plunger 19 relative to the housing 12. The viewing direction has been selected along the longitudinal axis 21 from the direction of the plunger 19.

The plunger 19 is shown in addition to the actuation element 29 with the ring 33, which surrounds the opening 32, and the arresting arrangement 36. Wall elements 42 radially delimiting the channel section 23 are illustrated on the plunger 19 and these support a wall 43, which has the end face (not illustrated). The bead 37 provided on the housing 12 is also shown.

Figure 5:
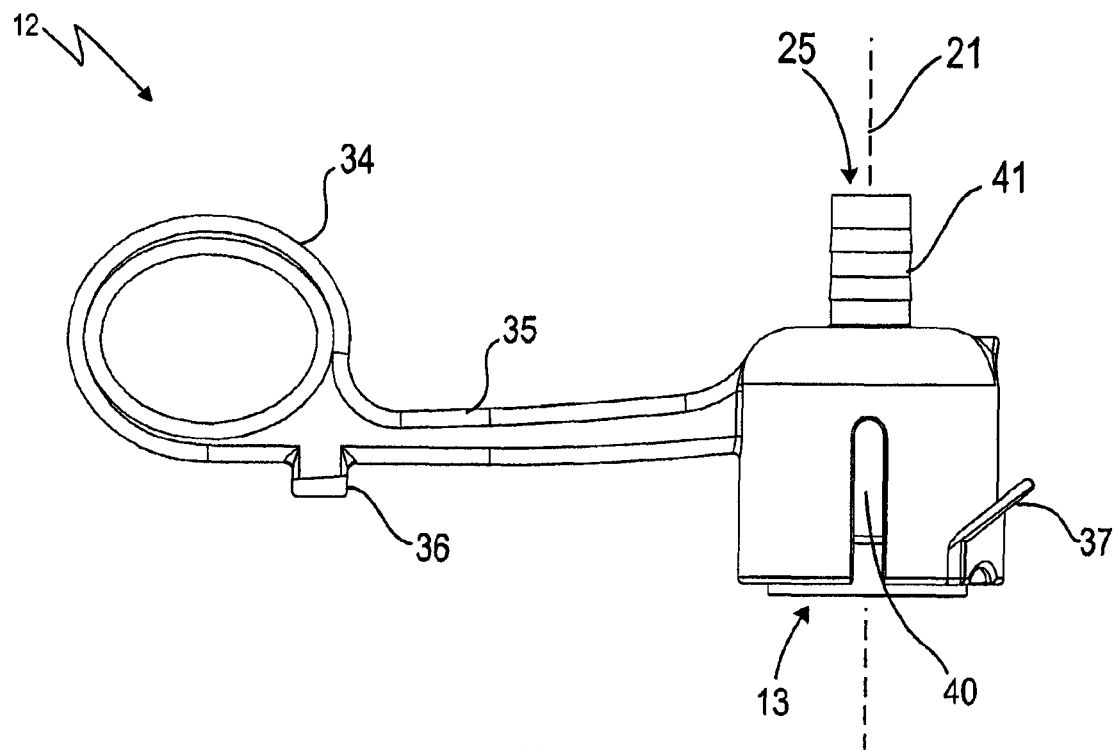
FIG. 5 shows a schematic illustration of an embodiment of the housing of the novel apparatus in a lateral view.

FIG. 5 shows a lateral view of a schematic illustration of the housing 12 of the novel apparatus 11. The housing 12 has the cup-shaped recess 13 and the grip 34, which is connected to the housing 12 via the arm 35.

The bead 37 serving as a support, the recesses 40 and the nozzle 41, which elongates and radially delimits the channel section 25, are furthermore provided on the housing 12.

Figure 6:
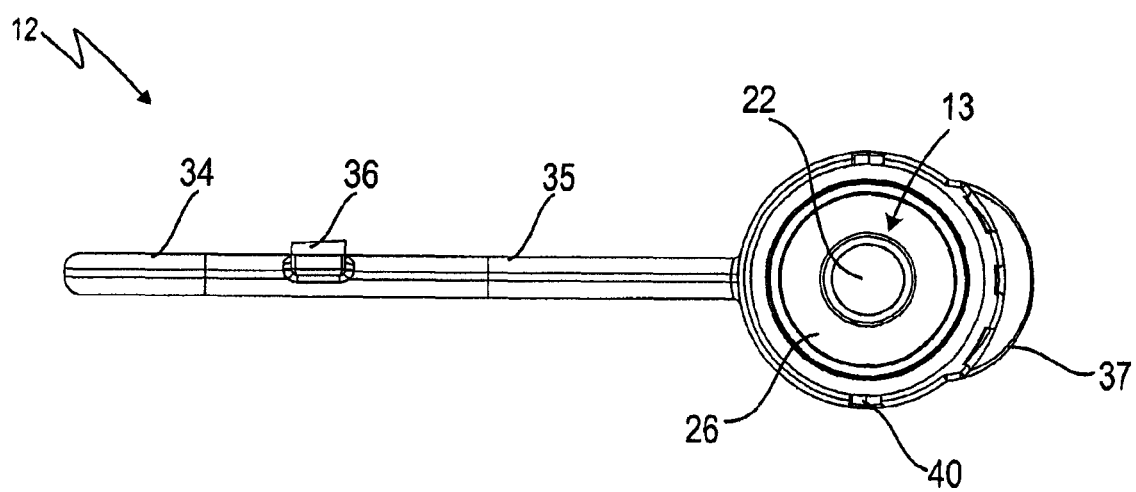
FIG. 6 shows a schematic illustration of the embodiment of the housing of the novel apparatus as per FIG. 5 in a plan view.

FIG. 6 shows a plan view of the housing 12 from FIG. 5. The viewing direction has been selected along the longitudinal axis 21 from the direction of the cup-shaped recess 13.

The housing 12 has the grip 34, which is connected to the housing 12 via the arm 35, the recesses 40, the bead 37 and the cup-shaped recess 13, the base 26 of which is penetrated by the channel 22.

Figure 7:
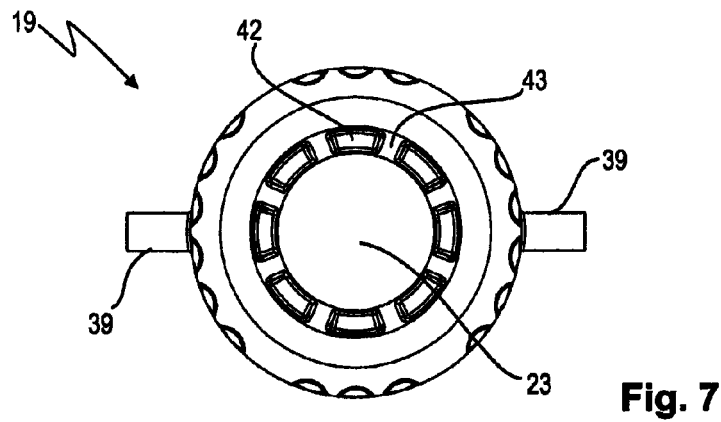
FIG. 7 shows a schematic illustration of an embodiment of the plunger of the novel apparatus in a plan view.

FIG. 7 shows a plan view of the plunger 19 of the novel apparatus 11.

The pins 39 for transferring the exerted force from the actuation element (not illustrated) to the plunger are provided on the plunger 19.

Furthermore, the wall elements 42 radially delimiting the channel section 23 are illustrated and these support the wall 43, which has the end face 20 (not illustrated).

Figure 8:
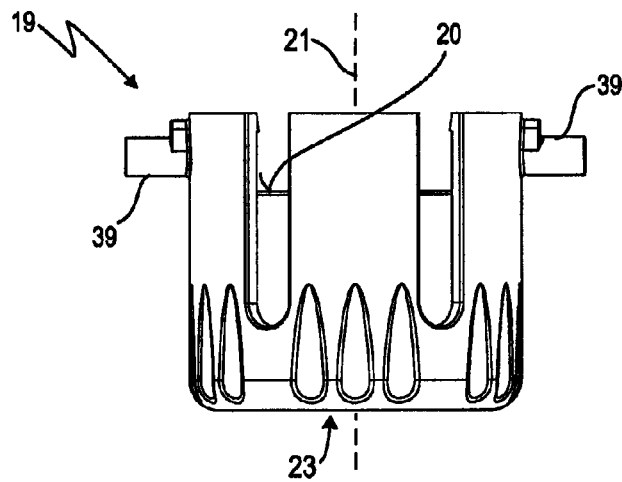
FIG. 8 shows a schematic illustration of the embodiment of the plunger of the novel apparatus as per FIG. 7 in a lateral view.

FIG. 8 shows a lateral view of the plunger 19 from FIG. 7 with the end face 20, the pins 39 and the channel section 23.

Figure 9:
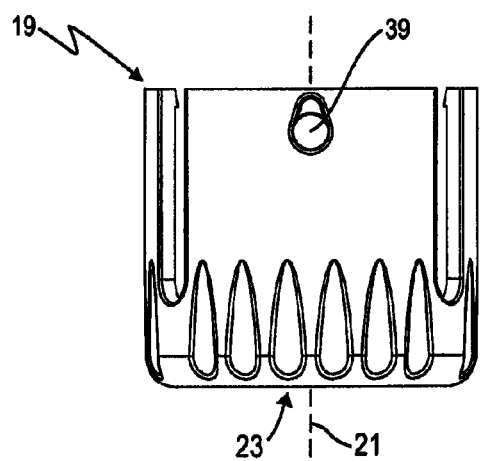
FIG. 9 shows a schematic illustration of the embodiment of the plunger of the novel apparatus as per FIG. 7 in a front view rotated by 90° with respect to FIG. 8.

FIG. 9 shows a front view of the plunger 19 from FIG. 7 with the pins 39 and the channel section 23.

Figure 10:
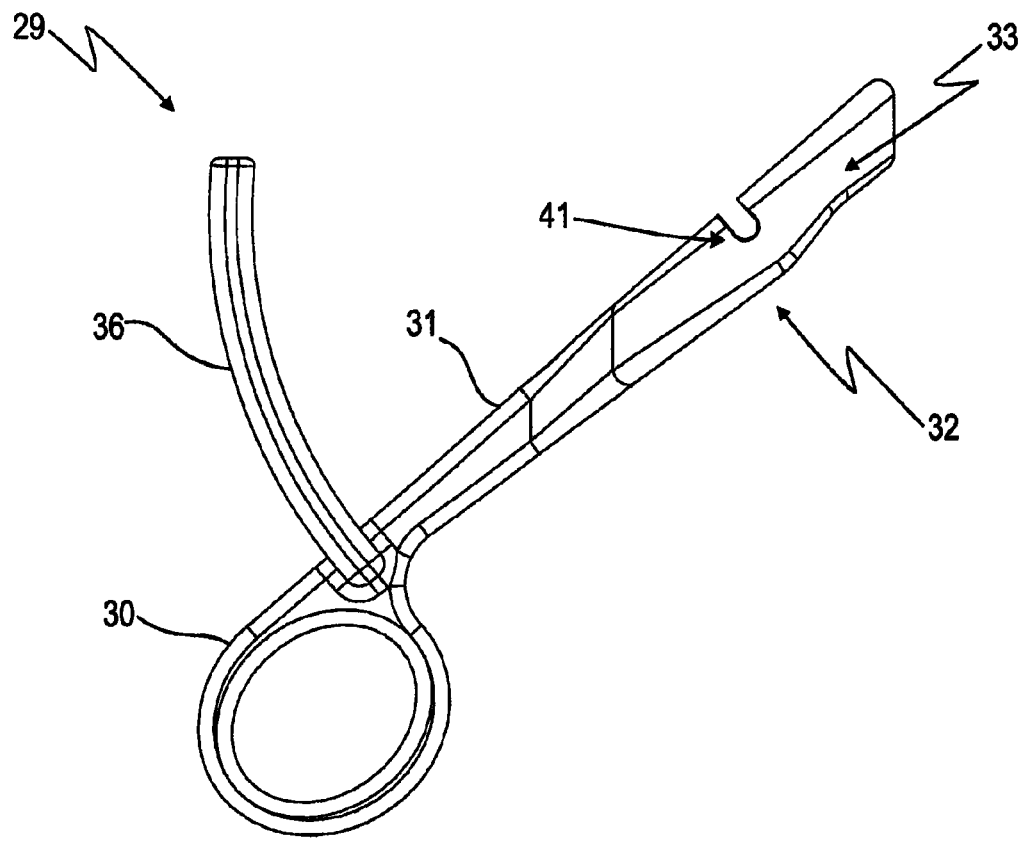
FIG. 10 shows a schematic illustration of an embodiment of the actuation element of the novel apparatus in a lateral view.

FIG. 10 shows a lateral view of the actuation element 29 with the grip 30, the latter being connected to the ring 33, which forms the opening 32, via the arm 31. The ring 33 surrounds the valve (not illustrated) in the circumferential direction. Part of the arresting arrangement 36 is furthermore provided on the arm 31.

The actuation element 29 furthermore has the recesses 38, in which the pins (not illustrated) of the plunger (not illustrated) are moveably held when the apparatus (not illustrated) is assembled.

The housing 12 moreover has the nozzle 41, which elongates and radially delimits the channel section 25.

Figure 11:
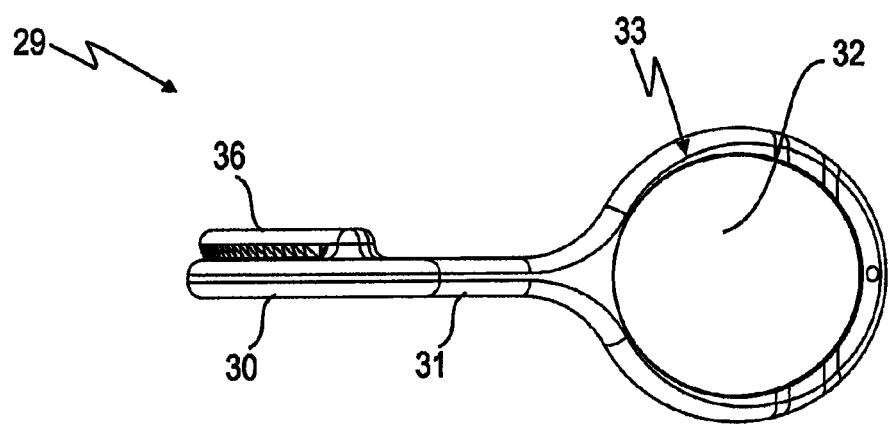
FIG. 11 shows a schematic illustration of the embodiment of the actuation element of the novel apparatus as per FIG. 10 in a front view rotated by 90° with respect to FIG. 10.

FIG. 11 shows a front view of the actuation element 29 from FIG. 10.

Figure 12:
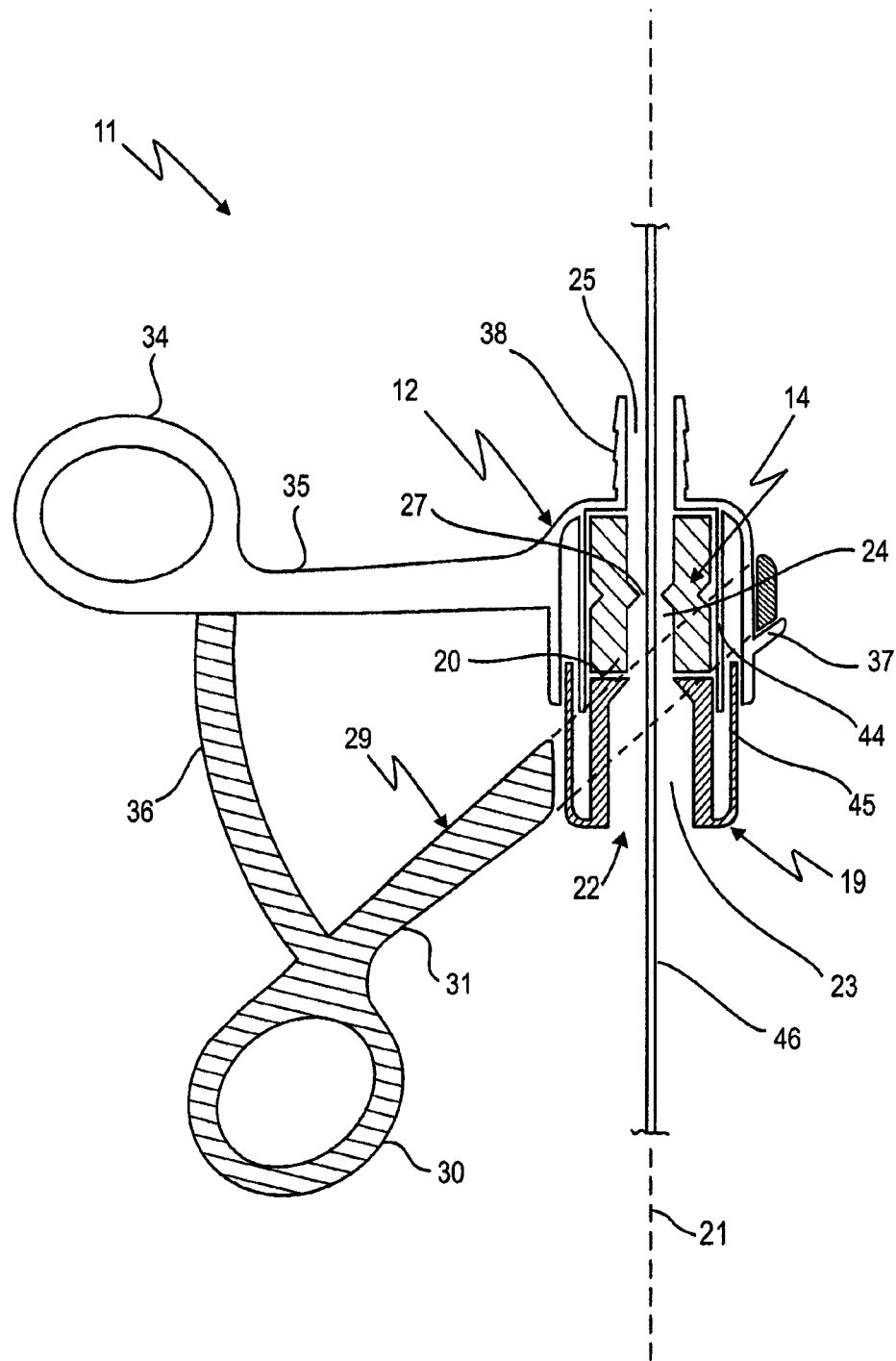
FIG. 12 shows a schematic illustration of an embodiment of the novel apparatus with an inserted catheter in a partly cut lateral view.

FIG. 12 shows a partly cut lateral view of a schematic illustration of an embodiment of the novel apparatus 11 with a catheter 46 routed through the channel 22.

Guide means 44 and 45 are shown on the plunger 19 and on the housing 12 and guide the plunger in the case of movement such that the plunger 19 is kept parallel to the longitudinal axis 21.

The catheter 46 is inserted into the channel 22 from the side of the plunger 19 and then passes through the channel section 23, the channel section 24 with the opening 27 and the channel section 25, which opens into a body cavity (not illustrated).

If the grips 30, 34 are now moved towards one another, the plunger 19 presses on the seal 14 with its end face 20; this leads to a narrowing of the opening 27 and seals the catheter 46 in the channel 22.

Therefore, what is claimed is:

1. An apparatus for inserting an elongated device into a body cavity, the apparatus having a valve, said valve having a longitudinal axis and comprising:
   a housing having a cup-shaped recess and a base, a first channel section provided in said base,
   a plunger having an end face, said plunger having at least its end face inserted into and displacable within the cup-shaped recess, a second channel section provided in the plunger, and
   a hollow cylindrical elastic seal arranged within the cup-shaped recess between said base and said end face, said seal having an outer face and an inner face defining there between a cross section of the seal, a third channel section provided in the seal and surrounded by the inner face,
   wherein the third channel section together with the first channel section and the second channel section forms a central channel, said central channel extending and being continuous along said longitudinal axis,
   said seal being provided with a change in said cross section in a region along said longitudinal axis; wherein a circumferential groove is provided on the outer face of the seal; and wherein means are provided for displacing said plunger along said longitudinal axis relative to said housing without changing the circumferential orientation of the plunger relative to the housing.

2. The apparatus of claim 1, wherein a circumferential web is provided on the inner face of the seal.

3. The apparatus of claim 2, wherein means are provided for displacing said plunger along said longitudinal axis relative to said housing without changing the circumferential orientation of the plunger relative to the housing.

4. The apparatus of claim 3, wherein said means for displacing said plunger comprise an actuation element, said actuation element connected to the plunger and provided with a first grip, and a second grip connected to the housing, said actuation element and said housing being moveably mounted in relation to one another.

5. The apparatus of claim 4, wherein each of said grips is provided on an arm arranged such as to act as a lever.

6. The apparatus of claim 5, wherein an arresting arrangement is provided for arresting said plunger in relation to the housing at least one position along the longitudinal axis.

7. The apparatus of claim 6, wherein the arresting arrangement is provided on the grips and the arms.

8. The apparatus of claim 4, wherein said actuation element is moveably arranged about at least one axis in relation to the plunger.

9. The apparatus of claim 3, wherein guide means are provided on the housing and the plunger, said guide means arranged for holding said plunger relative to the housing in a stable alignment parallel to said longitudinal axis.

10. The apparatus of claim 1, wherein a circumferential web is provided on the inner face of the seal.

11. The apparatus of claim 1, wherein said means for displacing said plunger comprise an actuation element, said actuation element connected to the plunger and provided with a first grip, and a second grip connected to the housing, said actuation element and said housing being moveably mounted in relation to one another.

12. The apparatus of claim 11, wherein each of said grips is provided on an arm arranged such as to act as a lever.

13. The apparatus of claim 12, wherein an arresting arrangement is provided for arresting said plunger in relation to the housing at least one position along the longitudinal axis.

14. The apparatus of claim 13, wherein the arresting arrangement is provided on the grips and the arms.

15. The apparatus of claim 11, wherein said actuation element is moveably arranged about at least one axis in relation to the plunger.

16. The apparatus of claim 1, wherein guide means are provided on the housing and the plunger, said guide means arranged for holding said plunger relative to the housing in a stable alignment parallel to said longitudinal axis.

17. The apparatus of claim 1, wherein the third channel section has a diameter of less than 10 mm.

* * * * *